(12) United States Patent
Wallach

(10) Patent No.: US 6,387,058 B1
(45) Date of Patent: May 14, 2002

(54) SELF-SAMPLING BRUSH AND METHOD FOR USE

(75) Inventor: Ronald M. Wallach, Westport, CT (US)

(73) Assignee: Wallach Surgical Devices, Inc., Orange, CT (US)

( * ) Notice: Subject to any disclaimer, the term of this patent is extended or adjusted under 35 U.S.C. 154(b) by 0 days.

(21) Appl. No.: 09/687,542

(22) Filed: Oct. 13, 2000

(51) Int. Cl.7 .............................................. A61B 10/00
(52) U.S. Cl. ....................................... 600/569; 600/572
(58) Field of Search ............................... 600/562, 569, 600/570, 572; 604/1, 327, 328, 330

(56) References Cited

U.S. PATENT DOCUMENTS

| | | | | |
|---|---|---|---|---|
| 4,023,559 A | * | 5/1977 | Gaskell | 600/572 |
| 4,157,709 A | * | 6/1979 | Schuster et al. | 600/572 |
| 4,175,008 A | | 11/1979 | White | 435/295 |
| 4,862,899 A | | 9/1989 | Bucaro | 128/749 |
| 4,953,560 A | | 9/1990 | Samuels | 128/759 |
| 5,121,752 A | | 6/1992 | Canna | 128/759 |
| 5,129,402 A | * | 7/1992 | Koll et al. | 600/572 |
| 5,339,828 A | * | 8/1994 | Keating et al. | 600/572 |
| 5,425,915 A | | 6/1995 | Phillips et al. | 422/58 |
| 5,445,164 A | | 8/1995 | Worthen et al. | 128/759 |
| 5,456,265 A | * | 10/1995 | Yim | 600/569 |
| 5,713,369 A | * | 2/1998 | Tao et al. | 600/569 |
| 5,787,891 A | | 8/1998 | Sak | 128/756 |
| 5,795,309 A | * | 8/1998 | Leet et al. | 600/569 |
| 6,013,036 A | | 1/2000 | Caillouette | 600/572 |
| 6,036,658 A | * | 3/2000 | Leet et al. | 600/569 |
| 6,059,735 A | * | 5/2000 | Sgro | 600/569 |
| 6,155,990 A | * | 12/2000 | Fournier | 600/572 |

* cited by examiner

*Primary Examiner*—Eric F. Winakur
*Assistant Examiner*—Charles Marmor, II
(74) *Attorney, Agent, or Firm*—Cummings & Lockwood

(57) ABSTRACT

A device is provided for self-sampling a body cavity, in particular the cervix, and a method is provided to use the device to obtain samples from the cervix for testing for the presence of human papillomavirus (HPV) DNA. The device includes elongated flexible bristles attached to a handle to form a mop-like sampling member. The sampling member is slidably disposed within an annular shield for insertion into the vaginal cavity and for positioning in contact with the cervix. After the shield is located in position, the shield is partially withdrawn to expose the elongated bristles to the cervix. The sampling member is rotated to mop the cervix and obtain a sample of cervical cells on the elongated bristles. The sampling device is then withdrawn from the vaginal cavity and the sample is sent for analysis.

12 Claims, 2 Drawing Sheets

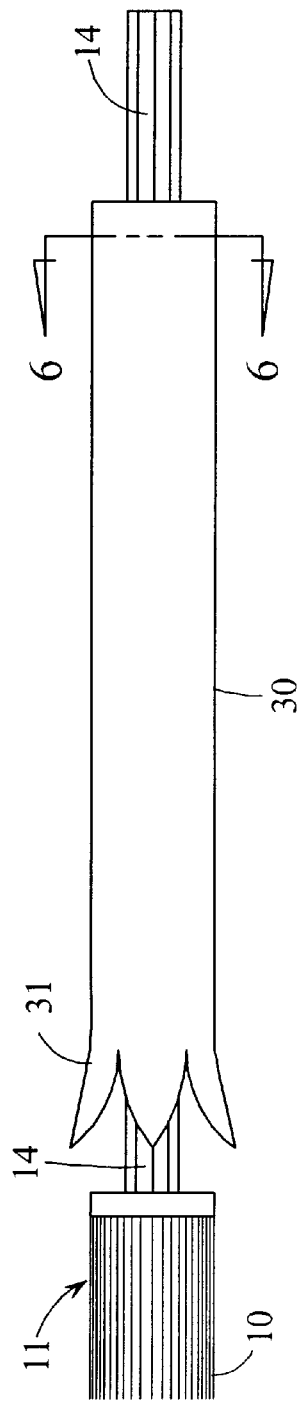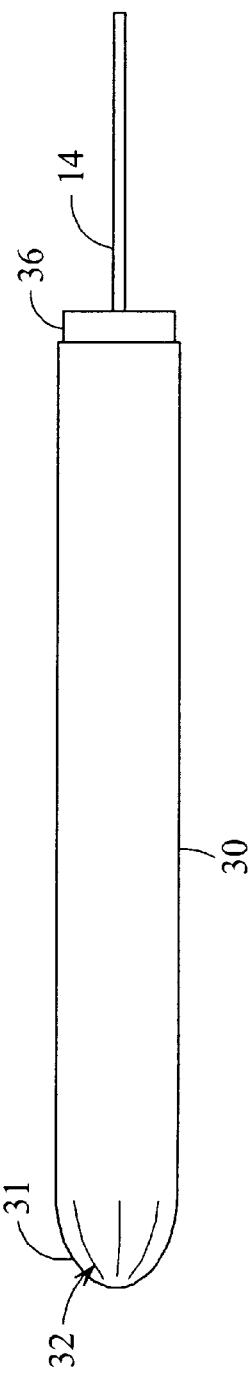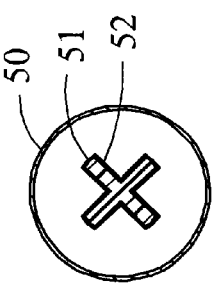

SELF-SAMPLING BRUSH AND METHOD FOR USE

FIELD OF THE INVENTION

The present invention relates to a self-sampling device which permits the obtainment of samples from body cavities and a method for using the device. In particular, the present invention permits women to self-sample to obtain cervical cells for testing for Human Papillomavirus DNA.

BACKGROUND OF THE INVENTION

Cytologic screening programs have been associated with dramatic reductions in the incidence of cervical cancer in certain parts of the world. Cytologic screening typically involves obtaining a sample of cells or tissue from the cervix and testing the sample for the presence of cervical carcinoma cells. The most common method used for this testing is the Papanicolaou (Pap) smear. Pap smears are generally performed by a physician during gynecological examination of the patient using sampling apparatus designed for use only by a physician. Due to the inconvenience, time and discomfort involved in having the Pap smear test performed by a physician, many women do not have the test performed at the recommended intervals. Also, in many countries, women do not have sufficient access to health care providers or health care facilities to have regular Pap smear testing performed. As a result, in these countries, cytologic screening to reduce the incidence of cervical cancer has not been successfully implemented.

Recent studies have shown that testing of samples of cervical cells for human papillomavirus (HPV) DNA can be used to screen for cervical disease. It has been reported that HPV DNA testing of clinician-obtained cervical samples has a sensitivity for detection of high-grade cervical squamous intraepithelial lesions and invasive cervical cancer that is equivalent or superior to that of a Pap smear. (Wright et al. 2000, HPV DNA testing of self-collected vaginal samples compared with cytologic screening to detect cervical cancer, Jour. Am. Med. Assoc. Vol. 283, No. 1). Clinician-obtained samples for HPV DNA testing have many of the same drawbacks as Pap smears, however, because the samples must be obtained by health care professionals and therefore are inconvenient, time consuming, uncomfortable, and may not be available to women in certain parts of the world.

Wright et al. have reported the results of studies showing that self-collected cervical cell samples can be used effectively for HPV DNA testing as a means of screening for women at high risk of having cervical disease. This screening can be used to identify women who should have more extensive testing performed. Accordingly, HPV DNA testing of self-collected samples can be used to identify women at high risk of having cervical disease in parts of the world where access to physicians or health care facilities is limited. Therefore, there is a need for a relatively easy and inexpensive means for self-collecting of samples to test for HPV DNA.

Prior devices used for collecting samples of cervical cells have several drawbacks and disadvantages. For example, many devices require a physician to collect the sample. Kist, U.S. Pat. No. 4,700,713, describes a sampling device comprised of bristles shaped to fit the cervix mounted on a handle, with each bristle having at least one longitudinal sharp edge. This device is intended for sampling only by a physician. Proper placement of the shaped bristles of the device with respect to the cervix must be effected by a physician during a gynecological examination and there is no means provided to guide the sampling device and assure proper placement to permit self-sampling.

White, U.S. Pat. No. 4,175,008, describes a culture specimen collection and transport device. The culture specimen collection portion of the device consists of a swab with an absorbent material at the end of the swab. There is no structure associated with the swab that would permit self-sampling of cervical tissue. Indeed, White states that his device is intended for use by physicians to obtain culture specimens, particularly of the ears, nose and throat. Accordingly, such a device could not be used for self-sampling.

Although several devices for self-sampling of the cervix have been developed, each of the devices has drawbacks and disadvantages. Canna, U.S. Pat. No. 5,121,752, describes a device for self-sampling to obtain PAP smear samples. A sample is obtained using a scraper head on a handle to scrape a sample from the cervix. A shaped speculum is used to insert the sampling device. In use, a hand mirror is required to locate the device properly to obtain a sample. This makes the device relatively difficult to use to obtain a sample. Also, the scraping action of the sampling portion of the device can cause discomfort, discouraging use of the device.

Other devices for self-sampling use absorbent swabs or other methods to collect the samples. For example Sak, U.S. Pat. No. 5,787,891, and Worthen, U.S. Pat. No. 5,445,164, describe self-sampling devices that use absorbent materials at the end of plunger type devices to absorb samples from the area of the cervix. These devices are relatively complicated in their design, rendering them more difficult to use and more expensive to manufacture. Also, relatively precise placement of the device is necessary to ensure a representative sample is obtained. The need for precise placement of self-sampling devices is a disadvantage, as it is difficult for a woman to ensure precise placement during self-sampling. In addition, absorbent material will take longer to release its captured specimen, and may not release all that it has absorbed. This can reduce the dependability of the test if the cells that are the subject of the test are more readily absorbed by the absorbent material.

Accordingly, the present invention overcomes one or more of the drawbacks or disadvantages of the prior art and provides an easy to use and inexpensive device to permit self-sampling of a body cavity, and in particular to permit self-sampling of the cervix to obtain a sample for testing for HPV DNA.

SUMMARY OF THE INVENTION

The present invention provides a device for self-sampling to obtain a sample of cells from the cervix to be tested for HPV DNA. In one embodiment, the device is comprised of a mop-like brush made of a plurality of elongated flexible bristles which are attached to a handle. The brush and handle are placed within an annular insertion shield. The distal end of the insertion shield is designed to assist in insertion of the sampling device into the vaginal cavity and in positioning the sampling device in the area of the cervix to obtain a sample of cervical cells.

After the sampling device is fully inserted within the vaginal cavity and the distal end of the insertion shield is located proximate to the cervix, the insertion shield is at least partially withdrawn, exposing the mop-like brush of the device to the cervix. The exposed mop-like brush is then rotated by the handle to obtain a sample of cells from the epithelium layer of the cervix adhering to the mop-like bristles of the brush. Due to the design of the mop-like brush, a representative sample of cells can be obtained without the need to locate the sampling device in an exact location relative to the cervix. After the sample has been collected, the handle is used to pull the mop-like portion back into the insertion shield and the sampling device is removed from the vagina. The mop-like brush containing the cell sample can then be tested to determine the presence of HPV DNA.

Among the advantages of the device is that a sample of cervical cells can be easily obtained by women without the intervention of a physician or health care professional. Accordingly, the time and expense involved in obtaining a sample is reduced. A further advantage of the invention is that the mop-like brush allows a representative sample of the cervix area to be obtained on the bristles of the mop-like brush without the need to locate the device precisely in relation to the cervix. Also, tests performed on samples obtained using non-absorbent material are more consistent than samples obtained on absorbent material. Accordingly, the sampling device is easy to use to obtain relatively accurate test results for HPV DNA.

DRAWING DESCRIPTION

So that those having ordinary skill in the art to which the subject invention appertains will more readily understand how to perform the method of the subject invention, reference may be had to the drawings wherein:

FIG. 4 is a schematic view of the closed ended insertion shield in use with the mop-like brush extended through the distal end of the insertion shield and in position for sampling.

FIG. 5 is a schematic view of a closed ended insertion shield containing an inner shield and a sample collecting member.

FIG. 6 is a cross-sectional view through line 6—6 in FIG. 4 of the proximal end of the insertion shield exhibiting a keyed opening therein which interlocks with similar protrusions on the handle of the sampling member to facilitate rotation thereof.

DETAILED DESCRIPTION OF THE PREFERRED EMBODIMENTS

The present invention is directed to a novel device for self-sampling to obtain a sample of cervical cells for HPV DNA testing. Preferred embodiments of the invention are described below in conjunction with the drawings provided herein. The preferred embodiments disclosed herein are to be considered exemplary of the principles of the present invention and are not intended to limit the invention to the embodiments described or illustrated. Various modifications will be apparent to those skilled in the art without departing from the scope or spirit of the invention disclosed herein.

Figure 1:
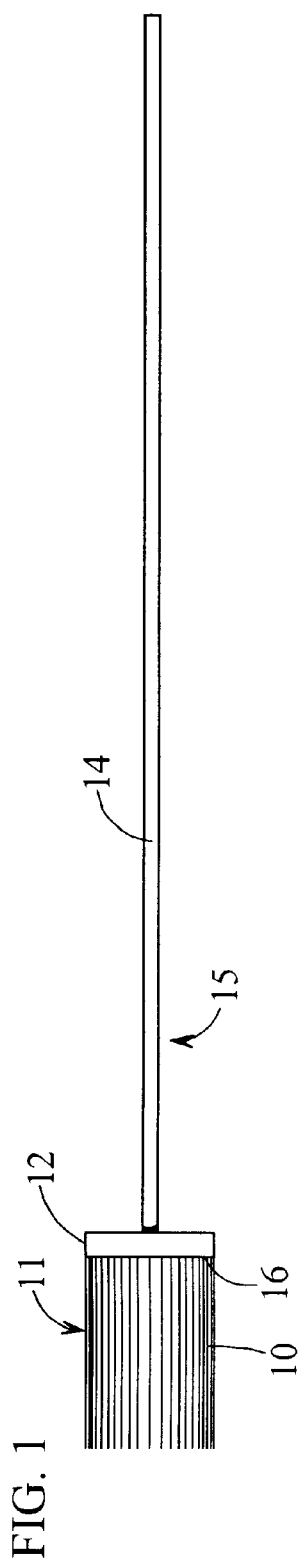
FIG. 1 is a schematic view of the mop-like brush and handle of the sampling device.

Referring now to the figures wherein like reference numerals identify similar structural elements of the subject invention, as illustrated in FIG. 1, in one embodiment of the invention, the device comprises a mop-like brush (10) with a plurality of bristles (11) extending from a base member (12). The bristles are preferably cylindrical in shape, and are of approximately uniform length. The bristles (11) and the base member (12) may be molded as one piece. Alternatively, the base member (12) may be molded with holes in the surface (16) of the base member to receive the bristles and the bristles are then inserted into the holes in the base member. The holes are preferably of a diameter approximately equal to the diameter of the bristles such that the bristles are retained in the base member by friction, or the bristles may be glued into the holes. The bristles of the mop-like brush are oriented substantially parallel to each other.

The base member (12) is attached to a handle (14) to form a sample collecting member (15). The handle (14) is press fit into a cavity in the end of the base member (12) opposite the bristles. The cavity in the end of the base member can be a keyed opening with the handle (14) shaped to fit closely within the keyed opening. The press fit between the handle and the base member should be such that the base member and bristles can be removed from the handle for sample analysis. Preferably the base member should be removable from the handle by applying a force to the base member of about three to six pounds.

The bristles of the mop-like brush can be made of any appropriate material known to one skilled in the art. The bristles are preferably made of a flexible plastic material such as, for example, polyethylene, polyurethane, polyvinyl chloride, polysiloxanes or nylon. The bristles are preferably at least one inch long and have a small diameter to be as flexible as possible. The tips of the bristles should be blunted to prevent puncture wounds. A long, slender design for the bristles increases the softness and surface area used for the mop-like sampling mechanism. To aid in molding, the bristles can be tapered with a smaller diameter at the tip of the bristle and a larger diameter at the base of the bristle.

An appropriate length for the bristles used in the mop-like brush may be determined using Euler's Formula, $$l = \pi \frac{IE}{4P}$$

where P is the total ultimate load in pounds, I is the least moment of inertia in inches$^4$, E is the modulus of elasticity of the material in pounds/inch$^2$, and I is the length in inches. Euler's formula is used for columnular structures which are so slender that bending or buckling action predominates and compressive stresses are not taken into account. Euler's formula can be used to determine a length for the bristles where they will bend or buckle, and thereby provide a mop-like brush. While the use of Euler's formula can aid in determining an appropriate length for the bristles, the invention is not limited to bristles whose lengths are determined by Euler's Formula or to any specific length for the bristles. The bristles may be any length provided that they are sufficiently long and flexible so as to form a mop-like brush.

The base member and handle may be made of any appropriate material known to one skilled in the art. The base member and handle are preferably made of a molded plastic such as, for example, polystyrene, polypropylene or nylon. Using a molded plastic allows the parts of the sample collecting member to be manufactured relatively inexpensively.

Figure 2:
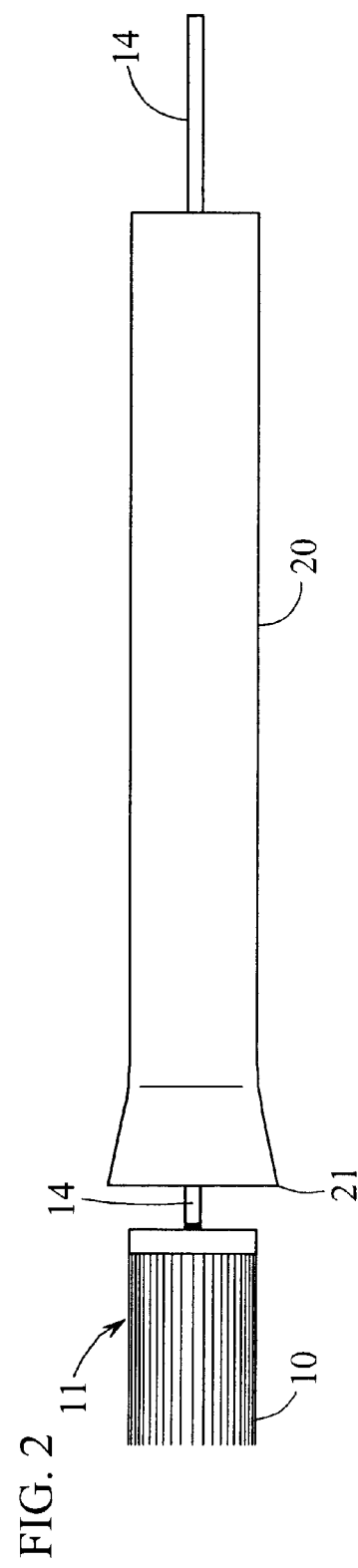
FIG. 2 is a schematic view of an insertion shield having a flared, open distal end, with the handle passing through the open distal end of the insertion shield and the mop-like brush extended beyond the open distal end of the insertion shield.

Referring to FIG. 2, the mop-like brush (10) and handle (14) are slidably disposed within a flared open ended annular insertion shield (20), such that the mop-like brush (10) is contained within the insertion shield (20) during insertion and removal from the vaginal cavity, and can be extended beyond the open distal end (21) of the insertion shield (20) for sampling. The insertion shield (20) is sized to allow relatively easy insertion into the vaginal cavity. The open distal end (21) of the insertion shield (20) is flared to allow easy insertion of the sampling device into the vaginal cavity and to assist the user in locating the sampling device in the area of the cervix. The handle (14) extends through the annular insertion shield (20) such that the handle (14) can be held and manipulated as necessary while samples are obtained. The insertion shield can be made of any appropriate material known to one skilled in the art. The insertion shield is preferably made of a molded plastic such as, for example, polystyrene, polypropylene or nylon.

In use, the insertion shield (20) containing the mop-like brush (10) is inserted into the vaginal cavity and the open distal end (21) of the insertion shield (20) is located in the area of the cervix. After the open distal end (21) has been placed in the proper location for sampling, the insertion shield (20) is partially withdrawn by sliding it along the handle (14). While the insertion shield is being partially withdrawn, the mop-like brush (10) is held stationary, causing the mop-like brush to extend beyond the flared open distal end (21) of the insertion shield (20) and exposing the mop-like brush (10) to the cervix. With the mop-like brush (10) in contact with the cervix, the sampling device is rotated using the handle (14), and a sample of cervical cells is obtained on the bristles (11) by the mopping action of the mop-like brush (10). The sampling device is preferably rotated at least two full revolutions in order to obtain a representative sample. The mopping action allows an adequate sample of cervical cells to be obtained without the need to precisely locate the mop-like brush in relation to the cervix.

After sampling is complete, the handle (14) is pulled backward to retract the mop-like brush (10) into the insertion shield (20). The insertion shield is removed from the vaginal cavity. The sampling device is then packaged for shipment to a laboratory for analysis for HPV DNA. In the preferred embodiment, the base member is removed from the handle and placed in a container with an appropriate solution. To avoid contamination of the sample, removal of the base member from the handle can be achieved using tweezers or an equivalent device. Alternatively, the insertion shield may include a stop in the interior of the annulus such that the base member can be pulled against the stop with sufficient force to remove the base member from the handle. The base member may then be dropped out of the insertion shield into the container. The container may contain a solution for preserving and fixation of the cells obtained on the bristles. An example of such a solution is described in Hurley, U.S. Pat. No. 5,256,271. Other appropriate solutions known to those skilled in the art may be used. After it has been removed from the handle and placed in an appropriate container, the base member can be shipped to a laboratory for analysis. If a solution is used in the container that permits results to be interpreted by the patient, the container may be retained by the patient for a predetermined period of time and the result interpreted by the patient.

Figure 3:
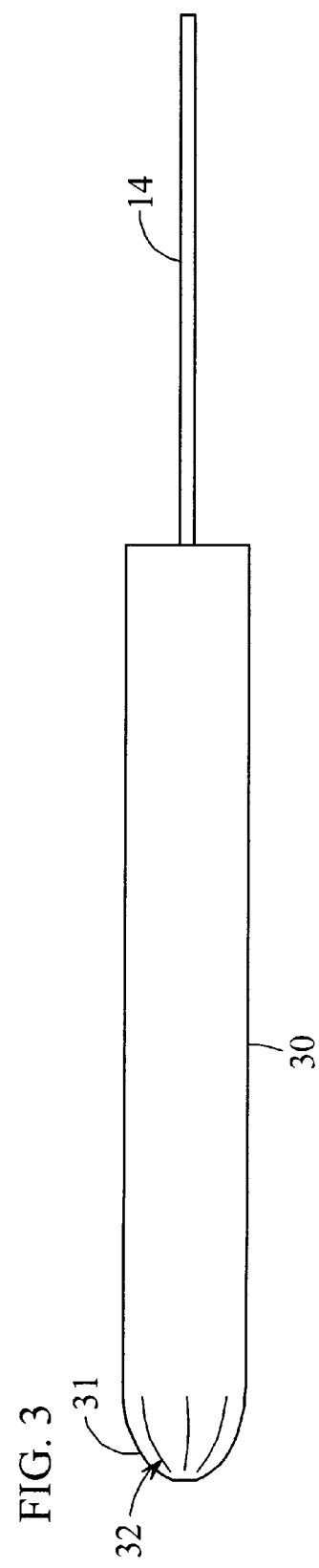
FIG. 3 is a schematic view of an insertion shield having a closed distal end.

In another embodiment of the sampling device, illustrated in FIG. 3, an annular insertion shield (30) is used to contain the mop-like brush on the sample collection member for insertion into the vaginal cavity. The arcuate distal end (31) of the insertion shield (30) is shaped to permit easy insertion into the vaginal cavity and to assist in locating the insertion shield proximate to the cervix. In this embodiment of the invention, the arcuate distal end (31) of the insertion shield (30) is normally closed. A plurality of slots (32) are cut into the arcuate distal end of the insertion shield such that the arcuate distal end (31) can be separated and opened upon application of force to the inside surface of the insertion shield (30). The slots can penetrate the material of the distal end of the insertion shield either fully or partially so long as the distal end can be opened upon application of force from the sample collection member. The number and shape of the slots can be varied as desired. The handle (14) and the mop-like brush are slidably disposed within the insertion shield (30).

In use, the insertion shield (30) containing the mop-like brush is inserted into the vaginal cavity and the arcuate distal end (31) of the insertion shield (30) is located proximate to the cervix. After the distal end (31) has been placed in the proper location for sampling, the insertion shield (30) is partially withdrawn by sliding it along the handle (14). While the insertion shield is being partially withdrawn, the handle (14) is held stationary, causing the mop-like brush to exert pressure on the inner arcuate surface of the distal end (31) of the insertion shield (30). As illustrated in FIG. 4, the slots on the distal end (31) of the insertion shield allow the distal end to open, exposing the mop-like brush (10) to the cervix. With the mop-like brush (10) in contact with the cervix, the sampling device is rotated using the handle (14), and a sample of cervical cells is obtained on the bristles (11) by the mopping action of the mop-like brush. The mopping action provides an adequate sample for testing without the need to precisely locate the mop-like brush in relation to the cervix.

After sampling is complete, the handle (14) is pulled backward to retract the mop-like brush (10) into the insertion shield (30). The insertion shield is removed from the vaginal cavity, and the sample is packaged for shipment to a laboratory for analysis or self-analyzed as discussed herein above.

In a further embodiment of the invention illustrated in FIG. 5, the annular insertion shield (30) is used to contain an inner shield (36) and the sample collection member. The arcuate distal end (31) of the insertion shield (30) is shaped to permit easy insertion into the vaginal cavity, and includes a plurality of slots (32) such that the arcuate distal end (31) can be separated and opened upon application of force to the inside surface of the insertion shield (30).

In using this embodiment of the invention, the insertion shield (30) containing the inner shield and the sampling member is inserted into the vaginal cavity, the insertion shield is pulled back over the handle, removed and discarded. The open distal end of the inner shield (36) is placed proximate to the cervix, and the inner shield is partially withdrawn by sliding It along the handle (14). This exposes the mop-like brush to the cervix. The sampling device is then rotated at least two full revolutions, and a sample of cervical cells is obtained.

After sampling is complete, the handle is pulled backward to retract the mop-like brush into the inner shield. The inner shield containing the sampling member are removed from the vaginal cavity, and the sample is packaged for shipment to a laboratory or self-analyzed as discussed herein above.

In a further embodiment of the invention, the insertion shield and sampling member handle may be adapted to allow rotation of the mop-like end of the sampling member by holding and rotating the insertion shield. In this further embodiment of the invention, the proximal end of the insertion shield is partially closed, for example by a plug or a cap. As illustrated in FIG. 6, the partially closed proximal end of the insertion shield (50) includes a keyed opening

(51) to permit the handle of the sampling member (52) to pass through the partially closed proximal end of the insertion shield (50). The keyed opening can be any shape that allows the insertion shield to engage and rotate the sampling member when the insertion shield is rotated. The handle of the sampling member (52) is shaped to fit closely within the keyed opening (51). After the insertion shield is located in position for sampling as described herein above, rotation of the mop-like brush is accomplished by holding and rotating the insertion shield. As the insertion shield is rotated, the handle of the sampling member (52) is engaged by the keyed proximal end of the insertion shield (50), causing the sampling member to rotate with the insertion shield.

The present invention and method for using the invention to obtain cervical cell samples overcomes the problem of requiring a physician to obtain samples for testing for HPV DNA. The mop-like brush used for sampling is capable of obtaining an adequate sample for testing without the need to precisely locate the mop-like brush in relation to the cervix. The mopping action results in sample from a relatively large area, making the device ideal for self-testing where precise location of the sampling device may not occur. Accordingly, the invention offers the advantages of being self-administered relatively easily, and it can be used for cytologic screening in areas where there is poor availability of physicians or other health care professionals.

The present invention is not limited to HPV DNA testing, and it may be used for obtaining samples from the cervix or vaginal cavity for other types of testing. Other uses for the sampling device of the present invention will be readily apparent to those of ordinary skill in the art. For example, the sampling device may be used for retrieval of samples in rape investigations, or in applications for obtaining samples from other body cavities.

As will be recognized by those of ordinary skill in the art based on the teachings herein, numerous changes and modifications may be made to the above-described invention without departing from its spirit or scope as defined in the appended claims. Accordingly, this detailed description of preferred embodiments is to be taken in an illustrative, as opposed to a limiting sense.

I claim:

1. A device for obtaining a sample from a body cavity, comprising:
    (a) a plurality of elongated flexible bristles of approximately uniform length connected to a handle to form a mop-like sample collecting member, said bristles being disposed in a direction substantially parallel to the axis of the handle; and
    (b) an annular insertion shield having a proximal end and a distal end, said sample collecting member being slidably disposed within said insertion shield such that the device is adapted for insertion into a body cavity, whereby the handle of said sample collecting member extends through the proximal end of the insertion shield and the elongated bristles on said sample collecting member are slid through and extended beyond the distal end of the insertion shield for obtaining a sample from a body cavity.

2. A device as claimed in claim 1, wherein said insertion shield has a flared, open distal end.

3. A device as claimed in claim 2, wherein the proximal end of said insertion shield includes a keyed opening, and said handle of said sample collecting member is shaped to fit closely within said keyed opening.

4. A device as claimed in claim 1, wherein said insertion shield has an arcuate distal end having a plurality of slots therein such that the arcuate distal end is opened upon application of force to the inner surface of said arcuate distal end.

5. A device as claimed in claim 4, further comprising an annual inner shield disposed with said insertion shield, said sample collecting member being slidably disposed within said inner shield, whereby the elongated bristles on said sample collecting member can be slid through and extented beyond the distal end of the inner shield for obtaining a sample from a body cavity.

6. A device as claimed in claim 4, wherein the proximal end of said insertion shield includes a keyed opening, and said handle of said sample collecting member is shaped to fit closely within said keyed opening.

7. A device as claimed in claim 1, wherein said elongated bristles are made of a plastic material selected from the group consisting of polyethylene, polyurethane, polyvinyl chloride, polysiloxanes or nylon.

8. A device as claimed in claim 1, wherein the proximal end of said insertion shield includes a keyed opening, and said handle of said sample collecting member is shaped to fit closely within said keyed opening.

9. A method for obtaining a cervical tissue sample from the vaginal cavity of a female human being, comprising the steps of:
    (a) providing a cervical sampling device including a plurality of elongated flexible bristles of approximately uniform length attached to a handle to form a mop-like sample collecting member, said bristles being disposed in a direction parallel to the axis of said handle, and said sample collecting member being slidably disposed within an annular insertion shield having an open distal end;
    (b) inserting said insertion shield into the vaginal cavity until the open distal end of said insertion shield is proximate to the cervix;
    (c) partially retracting said insertion shield to expose the bristles of said sample collecting member with said bristles of said sample collecting member contacting the cervix;
    (d) rotating said cervical sampling device such that said elongated bristles on said sample collecting member mop the cervix to collect a sample of cervical tissue;
    (e) retracting the handle of the sample collecting member while holding the insertion shield in place to retract said elongated bristles of said sample collecting member into said insertion shield;
    (f) removing said cervical sampling device from the vaginal cavity; and
    (g) submitting the collected cervical tissue sample for analysis.

10. The method of claim 9, further comprising the steps of:
    (h) disconnecting said flexible elongated bristles from said handle, and
    (i) placing said flexible elongated bristles in a container.

11. A method for obtaining a cervical tissue sample from the vaginal cavity of a female human being, comprising the steps of:
    (a) providing a cervical sampling device including a plurality of elongated flexible bristle of approximately uniform length attached to a handle to form a mop-like sample collecting member, said sample collecting member being slidably disposed within an annular insertion shield having a closed arcuate distal end, said closed arcuate distal end having slots therein such that the closed arcuate distal end can be opened upon application of force to the inner surface thereof;

(b) inserting said insertion shield into the vaginal cavity until the closed arcuate distal end of said insertion shield is proximate to the cervix;

(c) retracting said insertion shield to expose the bristles of said sample collecting member, said bristles of said sample collecting member contacting the cervix;

(d) rotating said cervical sampling device such that said elongated bristles on said sample collecting member mop the cervix to collect a sample of cervical tissue;

(e) retracting the handle of the sample collecting member while holding the insertion shield in place to retract said elongated bristles of said sample collecting member into said insertion shield;

(f) removing said cervical sampling device from the vaginal cavity; and (g) submitting the collected cervical tissue sample for analysis.

12. The method of claim 11, further comprising the steps of:

(h) disconnecting said flexible elongated bristles from said handle, and (i) placing said flexible elongated bristles in a container.

* * * * *